United States Patent [19]

Fraser-Reid et al.

[11] Patent Number: 4,514,561
[45] Date of Patent: Apr. 30, 1985

[54] PROCESS FOR PREPARING α-L N-ACETYL DAUNOSAMINIDE

[75] Inventors: Bertram Fraser-Reid, Silver Spring, Md.; Heinz W. Pauls, Durham, N.C.

[73] Assignee: Research Corporation, New York, N.Y.

[21] Appl. No.: 485,192

[22] Filed: Apr. 15, 1983

[51] Int. Cl.$^3$ ................................................ C07H 1/00
[52] U.S. Cl. ...................................... 536/18.7; 536/4.1; 536/17.2; 536/17.3; 536/124
[58] Field of Search ............... 536/6.4, 18.7, 53, 55.3, 536/17.2, 17.3, 124

[56] References Cited

U.S. PATENT DOCUMENTS 4,024,333  5/1977  Horton et al. .................. 536/18.7
4,067,969  1/1978  Penco et al. ..................... 536/6.4

OTHER PUBLICATIONS

Baker, et al., "Jour. Amer. Chem. Soc.", vol. 77, Jan. 1955, pp. 7–9.
Wong, et al., "Canadian Jour. Chem.", vol. 53, No. 20, 1975, pp. 3144–3145.

*Primary Examiner*—Johnnie R. Brown
*Attorney, Agent, or Firm*—Scully, Scott, Murphy & Presser

[57] ABSTRACT

The present invention is a unique method for the regioselective addition of a functional group to an allylic alcohol moiety which is particularly useful in the preparation of cis-hydroxyamino sugars.

1 Claim, 2 Drawing Figures

PROCESS FOR PREPARING α-L N-ACETYL DAUNOSAMINIDE

BACKGROUND OF THE INVENTION

The present invention, the discovery of which has been supported by the National Institute of Health, relates to the art of introducing functional groups to an allylic alcohol moiety, and, in particular, to an improved and efficient method for synthesizing compounds requiring stereospecific introduction of functional groups.

Preparation of compounds having not only particular adjunct chemical groups but also regulated structural positioning, has become of great interest in the area of organic synthesis. This is especially true with respect to the intensive research being conducted in antitumor chemotherapy. Limited positive results have been achieved in antitumor research by use of polychemotherapy in which different active substances are associated with known efficacious carrier substituents in a structurally regulated manner.

One of the predominant substituents is an amino sugar moiety. For example, U.S. Pat. Nos. 4,314,999 and 4,216,208 relate to N-acyl derivatives of an amino sugar with an oligopeptide. The antitumor chemotherapeutic activity of such compounds is reported in an article by DeBarbieri entitled "n-Acyl Derivatives of Glucosamine with Oligo-Peptides", *Current Chemotherapy*, American Society of Microbiology, p. 1183 (April 1978). The amino sugars listed therein as useful in the disclosed chemotherapeutic combination hexosamines, such as glucosamine, galactosamine, or mannosamine.

Other effective antitumor drugs include daunomycin and doxorubicin, which is available as doxorubicin hydrochloride from Adria Laboratories, Inc. under the trade name Adriamycin. Daunomycin consists of the aglycone daunomycinone and the amino sugar, daunosamine. Similarly, doxorubicin consists of the aglycone adriamycinone and daunosamine.

Techiques for synthesizing doxorubicin and daunomycin, and their aglycones, adriamycinone and daunomycinone, are known. See, e.g., Wong, et al., Canadian Journal of Chemistry, Vol. 51, p. 466 (1973); Acton, et al., Journal of Medicinal Chemistry, Vol. 17, No. 6, p. 659 (1974); Kende, et al., Journal of American Chemical Society, Vol. 97, No. 15, p. 4425 (1975) and Vol. 98, No. 7, p. 1967 (1976); and Kende, et al., U.S. Pat. No. 4,021,457. Techniques for attaching daunosamine to the aglycones are also known. See, e.g., Acton, et al., supra, and Smith, et al., Journal of American Chemical Society, Vol. 98, No. 7, p. 1969 (1976). Furthermore, it is well known how to synthesize the aglycones adriamycinone and daunomycinone.

However, while techiques for synthesizing daunosamine are known, the known techniques suffer severe shortcomings that limit their practical utility. For example, the process disclosed in Marsh, et al., Chemical Communications, p. 973 (1967) uses a difficult method to obtain glycal as a starting material and involves the use of a potentially hazardous step of making an azide derivative with sodium azide. Furthermore, in the process disclosed by Marsh, et al., isomers are produced that require separation by a difficult chromatographic step. The process disclosed in Horton, et al., Carbohydrate Research, Vol. 44, p. 227 (1975), requires the use of a number of very expensive reagents and also results in the production of difficult to separate isomers.

U.S. Pat. No. 4,301,276 describes a technique for synthesizing daunosamine hydrochloride and intermediates which can be converted into daunosamine hydrochloride from either L-fucal produced by a rather lengthy synthesis from D-galactose or D-glucose or 6-deoxy-L-idal which also requires a lengthy process. Similarly, U.S. Pat. No. 4,181,795 shows an involved process for synthesizing daunosamine and related compounds, and U.S. patent application Ser. No. 128,298, now U.S. Pat. No. 4,298,726, discloses, inter alia, a process for synthesizing alkyl L-ristosamides and N-benzoyl-L-ristosamine, ristosamine being a configurational analog of daunosamine.

In U.S. Pat. No. 4,024,333 a method of synthesizing daunosamine is shown characterized by conversion of a D-mannose starting material into a 2-deoxy-3-keto intermediate whose oxime is reduced with high stereoselectivity to introduce the correctly oriented D-ribo-3-amino group, followed by a stereospecific step late in the sequence to introduce the terminal C-methyl group with inversion at C-5, to generate the required L-lyxo stereochemistry.

None of the known techniques for the synthesis of the anthracycline antibiotics has been proven to be commercially successful, however, due to difficulties encountered, inter alia, properly oriented hydroxyamination of the amino sugars. By the present invention, however, the above-described problems have been overcome to a significant degree.

BRIEF DESCRIPTION OF THE INVENTION

The present invention relates to the regioselective introduction of functional groups to an allylic alcohol moiety which involves an electrophile-induced cyclization of the hydroxy-bearing carbon atom with the adjacent double-bonded carbon atom. Specifically, the synthesis of the present invention provides an efficient process for stereospecific hydroxyamination, preferably the cis-hydroxyamination of a cyclic sugar moiety containing an allylic alcohol moiety.

In regard to the preferred embodiment of the present invention, inexpensive cyclic sugar starting materials can be cis-hydroxyaminated with relative ease and efficiency by the stereospecific introduction of the functional amine group to the allylic alcohol moiety in the sugar ring. In many cases it is necessary to convert an oxygen-containing adjunct such as hydroxy from one side to the other, i.e., to convert the starting allylic alcohol to its epimer. In general this may be achieved, for example, by a Walden inversion. One such process is known as the Mitsunobo reaction, which results in an inverted benzoate ester. After inversion of the allylic oxygen, the corresponding inverted hydroxy, i.e., free alcohol, can be recovered by saponification of the ester resulting from such inversion.

The inverted free hydroxyl group can then be converted to an imidate ester, for example, by addition of acetonitriles, especially trichloroacetonitrile. In the preferred mode, the double bond adjacent to the inverted-hydroxy-bearing carbon atom is then attacked with an electrophile. It has been found that iodine dicollidine perchlorate is especially effective in this role because iodine is easily added and easily removed.

This electrophilic attack on the double bond allows the electron-rich nitrogen of the pendant imidate ester to cyclize at said adjacent carbon atom. The resulting cyclized imidate ester can then be reduced by appropriate means to form the cis-hydroxy-amino sugar. Such reduction can be performed by hydrogenolysis using a mixture of tri-n-butyl tin hydride and azo-bis-isobutyronitrile in anhydrous benzene, and then hydrolysis in an aqueous solution of paratoluenesulfonic acid and pyridine.

As a result of this process accurate stereospecific configuration of hydroxy and amino groups can be achieved with a high degree of efficiency. In particular, the present synthesis can be applied to the troublesome cis-hydroxyamination of cyclic sugar moieties.

Further, the present mechanism is readily adapted to industrial scale synthesis of daunosamine, the amino sugar moiety of the most widely used anti-cancer agents, as well as to the production of other cis-hydroxy-amino sugars which can be used, for example, in chemotherapeutic agents.

For a better understanding of the present invention, together with other and further objects, reference is made to the following description, taken in conjunction with the accompanying drawings, and its scope will be pointed out in the appended claims.

DESCRIPTION OF THE PREFERRED EMBODIMENTS

Figure 1:
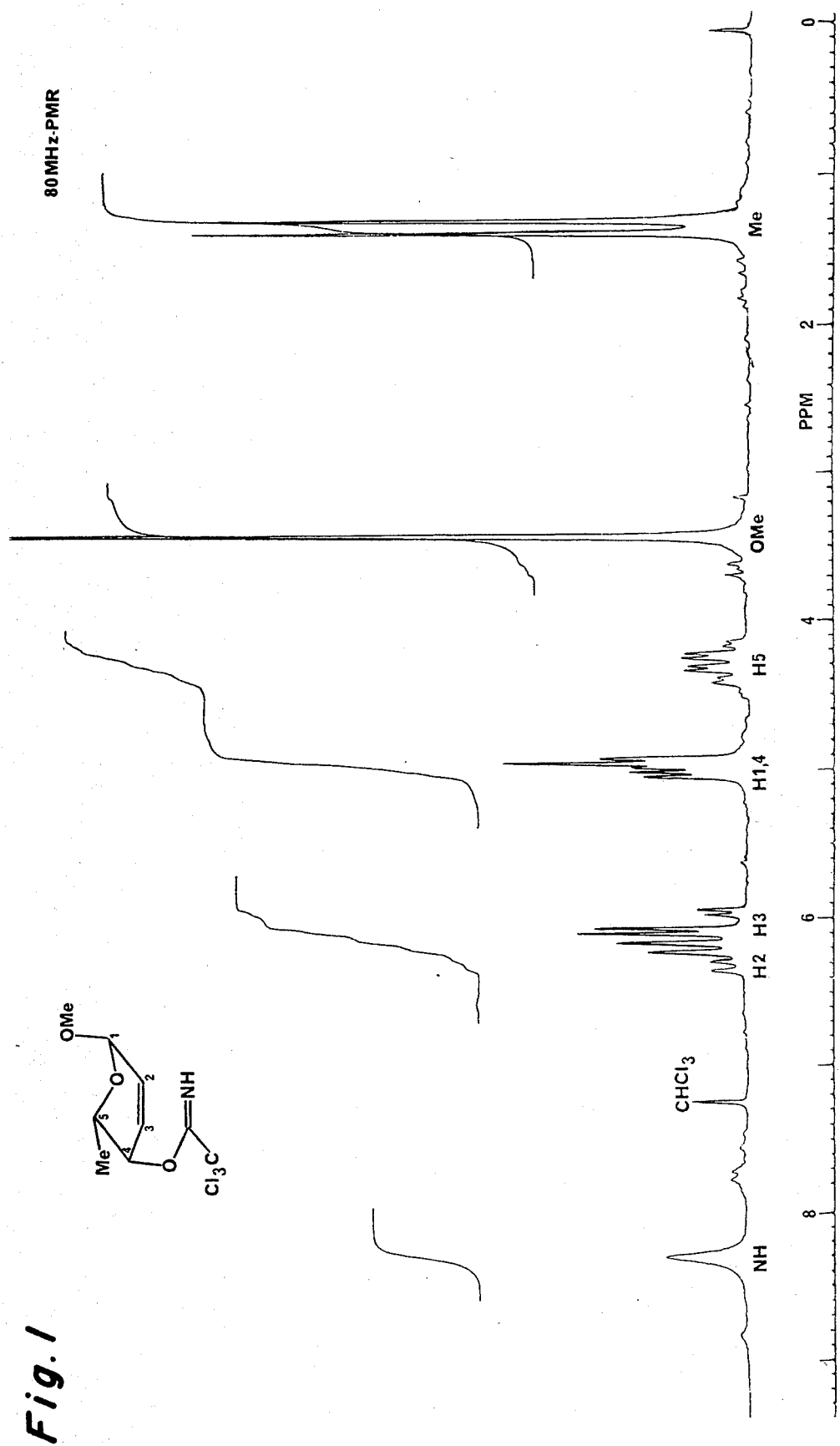
FIG. 1 is a representative nuclear magnetic resonance (NMR) spectrum which confirms that the intermediate bears the required imidate ester.

In the process of the present invention the starting material contains an allylic hydroxyl group, i.e., an allylic alcohol moiety,

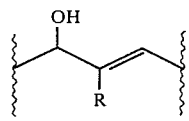

wherein R is H or alkyl. While such material can be a straight chain organic compound, the preferred process contemplates use of a cyclic sugar compound having an unsaturated carbon-carbon bond which forms the allylic alcohol moiety. A particularly convenient starting material has been found to be the unsaturated cyclic hemiacetal form of rhamnose (the 6-deoxy analog of mannose),

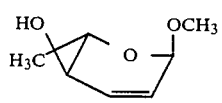

which is commercially available from suppliers such as Pfanstiehl Labs, Inc., Waukegan, Illinois. Such starting materials are readily available, and are considered particularly useful in the present process especially in adaptation of the synthesis to an industrial scale since sugar compounds exist in both the crystalline state and in solution in the cyclic hemiacetal form.

In order, however, to introduce an amino group for stereoselective addition to the cyclic sugar compound, the allylic hydroxy group is inverted to the epimer of the original allylic hydroxy by means of, for example, a Walden inversion.

The Mitsunobo reaction is an example of such conversion wherein the starting compound is reacted with benzoic acid in the presence of diethyl-azo-dicarboxylate (DEAD),

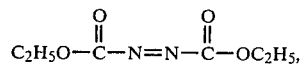

and triphenyl phosphine,

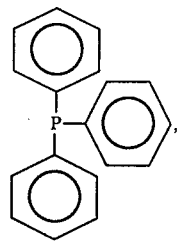

in anhydrous tetrahydrofuran (THF). The reaction is run at a reduced temperature of from about $-10°$ C. to about 5° C., and preferably at about 0° C., for a time of from about 30 minutes to about 10 hours, and preferably 1 to about 5 hours. As a result of this treatment the allylic hydroxy forms the benzoate ester in the inverted position,

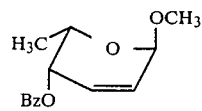

wherein Bz is benzoic acid.

This resulting ester is saponified with an organic metal salt such as sodium methoxide and an alcohol such as methanol at a temperature of from about 15° to about 30° C., preferably about 23° C., for a time period of from about 3 to about 18 hours, and preferably from about 5 to about 12 hours, to form the inverted free allylic alcohol,

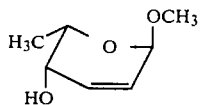

The free allylic hydroxy group is then converted to an imidate ester or like compound capable of directing an amino group to the adjacent double-bonded carbon atom in a cis configuration to the sugar ring. Such compounds presently include, but are not limited to, halogenated acetonitriles. In the present process it was found that when trichloroacetonitrile ($Cl_3C-C\equiv N$) was introduced along with sodium hydride and methylene chloride to the sugar having the inverted allylic hydroxy group at a temperature of from about $-5°$ C. to about 5° C., preferably at about 0° C., and allowed to warm to about room temperature by holding in its reaction container for a time of from about 1 to about 8 hours, but preferably for about 3 hours. The following intermediate imidate ester is formed

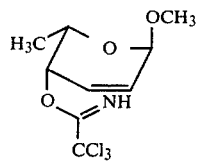

which is a precursor intermediate that directs the amino group regioselectively to the adjacent double-bonded carbon atom in the cis configuration relative to the oxygen atom of the imidate ester.

Cyclization of the imidate ester is completed by attacking the unsaturation of the allylic moiety with an electrophile in order to allow the electron-rich nitrogen to form a bond with the carbon atom adjacent the inverted hydroxy-bearing carbon atom. It is important to choose an electrophile that is readily attached and easily removed so that the cyclized imidate ester is readily formed without the likelihood of rupture upon removal of said electrophile. Electrophiles which may be considered for such use include, but are not limited to, halogen electrophiles such as molecular iodine ($I_2$), mercuric ion, and, in particular, iodine dicollidine perchlorate, I (collidine)$_2$ ClO$_4$. It was found that this latter electrophile, which is especially effective, is advantageously introduced in an acetonitrile solution at a temperature of from about 15° C. to about 28° C., preferably from about 20° C. to about 25° C., for a period of from about 2 to about 6 days and preferably about 4 days. The cyclized intermediate resulting from treatment with iodine dicollidine perchlorate has the formula

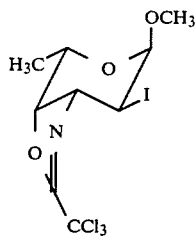

After the cyclized imidate ester intermedate is produced it is subjected to hydrogenolysis by reacting it in a mixture of tri-n-butyl tin hydride, azo-bis-isobutyronitrile in anhydrous benzene with heating at reflux for a time of from about 1 to about 5 hours, and preferably about 3 hours. The halogens were replaced with hydrogen as shown below:

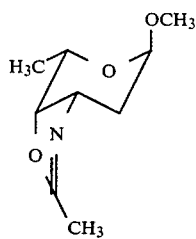

This preparation is followed by hydrolysis of the intermediate in an aqueous mixture containing para-toluenesulfonic acid and pyridine at a temperature of from about 20° C. to about 120° C., preferably at about 100° C., for about 1 to about 5 hours, and preferably for about 2.5 hours. Hydrolysis of the cyclized intermediate results in a cis hydroxy amino sygar compound of the following structure

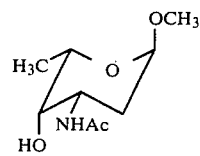

wherein Ac is acetyl,

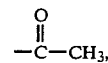

which is methyl alpha-L N-acetyl daunosaminide, a daunosamine derivative in an enantiomerically pure form.

EXAMPLE

A six-step synthesis was carried out in accordance with the above-described protocol as follows:

(a) A sample of methyl 2,3-dideoxy-alpha-L-erythrohex-2-enopyranoside, prepared from L-(+)-rhamnose (from Pfanstiehl Laboratories, Inc.) was reacted with benzoic acid, in the presence of diethyl azo dicarboxylate and triphenylphosphine in an anhydrous tetrahydrofuran solution at 0° C. for about 2.5 hours, to invert the allylic hydroxy group.

(b) The product from step (a) was then treated with sodium methoxide and methanol at room temperature, e.g., 23° C., for about 8 hours to obtain the free hydroxyl from the inverted benzoate ester.

(c) In order to convert the free hydroxyl to the imidate ester, trichloroacetonitrile was reacted in the presence of sodium hydroxide and methylene chloride at about 20° C. for 3 hours, the resulting product having a syrupy consistency. This intermediate was isolated and tested to determine its structure. An actual nuclear magnetic resonance (NMR) spectrum, representative of several such analytical runs, is shown at FIG. 1, which is discussed hereinbelow.

Figure 2:
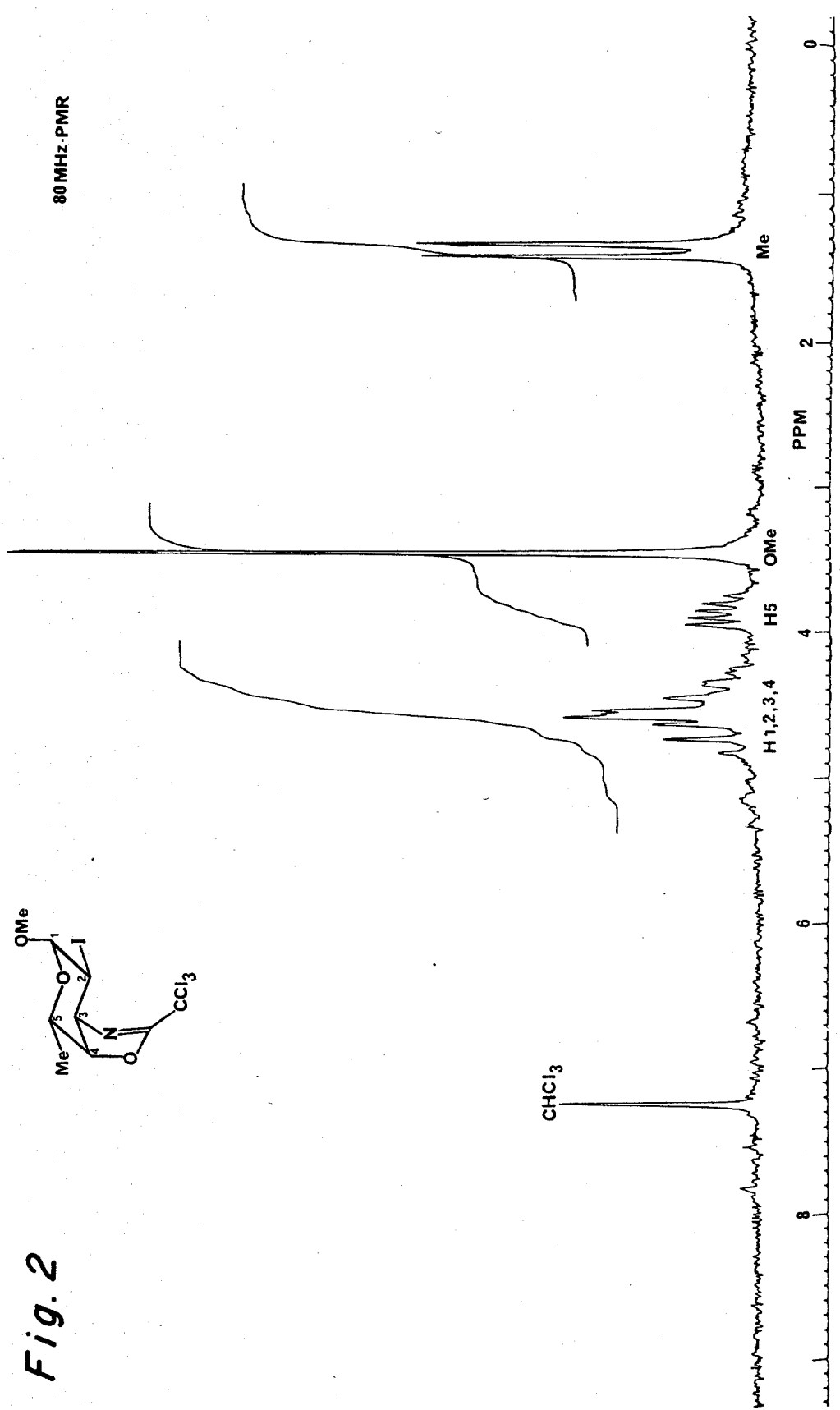
FIG. 2 is a representative nuclear magnetic resonance (NMR) spectrum which confirms the presence of the cyclized imidate ester in the intermediate.

(d) Cyclization of the imidate ester was then effected by reacting iodine dicollidine perchlorate with the imidate ester in an acetonitrile solution at room temperature, approximately 23° C. for about 4 days. The product from this reaction was crystalline. Identity of the product was established by elemental analysis and NMR spectra, a representative spectrum of which is shown in FIG. 2. A discussion of the results follows the present Example.

(e) After cyclization, the halogens were removed by hydrogenolysis carried out reacting the product with tri-n-butyl tin hydride and azo-bis-isobutyronitrile in an anhydrous benzene solution while refluxing for about 3 hours.

(f) The dehalogenated cyclized intermediate was then hydrolyzed with para-toluenesulfonic acid and pyridine in an aqueous solution at about 100° C. for about 2.5 hours.

The product recovered was an enantiomerically pure daunosamine derivative, alpha-L N-acetyl daunosaminide, which is a ready source of daunosamine,

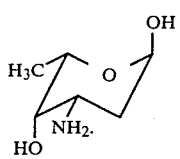

The process resulted in a 60% overall yield.

Analytical tests were conducted to confirm the structure of the imidate ester intermediate and the cyclized intermediate. Elemental analysis, infrared spectra (IR) and nuclear magnetic resonance (NMR) spectra were obtained confirming the structures disclosed herein. One of the best indicators of the structures is the NMR spectrum which indicates the different types of protons (hydrogen atoms), as well as the relative number thereof in a given molecule by reading the strength of the magnetic field at which the different protons absorb the energy required to "flip" the proton to a less stable alignment against a magnetic field.

The different levels at which the different protons attain a higher energy state are indicated by absorption peaks which can be compared to a standard for purposes of identification.

NMR spectra resulting from the products, intermediate or otherwise, of the above example were compared with literature examples, e.g., L. A. Overman, *J. Am. Chem. Soc.*, 1976, 98,2901; Y. Yamamoto, H. Shimoda, I. Oda and Y. Inouye, *Bull. Chem. Soc. Jpn.*, 1976, 49, 3247.

Thus, in FIG. 1, the peaks are identified as indicated therein as representative of each of the type of protons found in the imidate ester intermediate resulting from step (c) in the Example. Furthermore, FIG. 2 shows peaks which identify each of the type of proton found in the cyclized imidate ester resulting from step (d).

These spectra as well as IR spectra and elemental analysis provide sufficient proof of the existence of the intermediates.

Moreover, similar identifying analyses (spectroscopic, optical rotation, melting points, etc.) were run to provide identifying indicia for the end products sufficient to satisfactorily verify that daunosamine was, indeed, the ultimate product. Among other things, the following elemental analysis compared sufficiently close in value to the theoretical to give basis for proper identification.

| ELEMENTAL ANALYSIS OF END PRODUCT | | |
|---|---|---|
|  | Theoretical Percentage by Molecular Weight | Percentage by Molecular Weight Found Experimentally |
| Carbon: | 26.08% | 26.33% |
| Hydrogen: | 2.68% | 2.67% |
| Nitrogen: | 3.38% | 3.53% |

As can be seen the differences of all values from the theoretical is less than 0.4% which is considered adequate for purposes of valid identification.

Thus, while there has been disclosed what are presently believed to be the preferred embodiments of the present invention, those skilled in the art will understand that changes and modifications may be made thereto without departing from the true spirit of the invention, the scope of which is pointed out in the appended claims, and it is intended to claim all such modifications as fall within the true scope of the invention.

What is claimed is:

1. A method for the synthesis of methyl alpha-L N-acetyl daunosaminide of the formula:

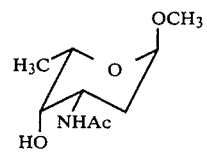

which comprises the steps of:
(a) reacting methyl 2,3-dideoxy-alpha-L-erythrohex-2-enopyranoside with benzoic acid to invert the allylic hydroxy group;
(b) treating the resulting product to obtain the free hydroxyl group from the inverted benzoate ester;
(c) converting the free allylic hydroxy group to the corresponding imidate ester;
(d) cyclizing the resulting imidate ester;
(e) subjecting the cyclized imidate ester to hydrogenolysis to replace the halogen atoms with hydrogen atoms; and
(f) thereafter hydrolyzing the resulting dehalogenated cyclized imidate ester to give methyl alpha-L N-acetyl daunosaminide.

* * * * *